(12) United States Patent
Unal et al.

(10) Patent No.: US 12,103,171 B2
(45) Date of Patent: Oct. 1, 2024

(54) CHAIRLESS CHAIR EXOSKELETON

(71) Applicant: OZYEGIN UNIVERSITESI, Istanbul (TR)

(72) Inventors: Ramazan Unal, Istanbul (TR); Ozgur Karaoglan, Izmir (TR)

(73) Assignee: OZYEGIN UNIVERSITESI, Istanbul (TR)

( * ) Notice: Subject to any disclaimer, the term of this patent is extended or adjusted under 35 U.S.C. 154(b) by 106 days.

(21) Appl. No.: 18/012,993

(22) PCT Filed: Dec. 30, 2020

(86) PCT No.: PCT/TR2020/051456
§ 371 (c)(1),
(2) Date: Dec. 27, 2022

(87) PCT Pub. No.: WO2022/146251
PCT Pub. Date: Jul. 7, 2022

(65) Prior Publication Data
US 2023/0234214 A1   Jul. 27, 2023

(51) Int. Cl.
| | |
|---|---|
| *A47C 9/02* | (2006.01) |
| *B25J 9/00* | (2006.01) |
| *A61F 5/01* | (2006.01) |
| *A61G 5/14* | (2006.01) |
| *A61H 1/02* | (2006.01) |

(52) U.S. Cl.
CPC .......... *B25J 9/0006* (2013.01); *A47C 9/025* (2013.01); *A61F 5/0125* (2013.01); *A61G 5/14* (2013.01); *A61H 1/024* (2013.01)

(58) Field of Classification Search
CPC .......... A47C 9/025; A47C 9/027; A47C 9/10; A61F 5/0125; A61G 5/14; A61H 1/024; A61H 3/00; B25J 9/0006
See application file for complete search history.

(56) References Cited

U.S. PATENT DOCUMENTS

| | | | | |
|---|---|---|---|---|
| 4,138,156 A | * | 2/1979 | Bonner | A47C 9/10 297/DIG. 10 |
| 10,271,660 B2 | * | 4/2019 | Gunura | A61F 5/0125 |
| 10,537,459 B2 | * | 1/2020 | Gunura | A47C 9/025 |

(Continued)

FOREIGN PATENT DOCUMENTS

| | | |
|---|---|---|
| CN | 105250117 A | 1/2016 |
| EP | 3318240 A1 | 5/2018 |

OTHER PUBLICATIONS

Invisible Chair Trick Revealed, Magic, dArtofScience, Jul. 29, 2016, (2:14'-3:57') https://www.youtube.com/watch?v=Up_SOfxsdHo.

*Primary Examiner* — Syed A Islam
(74) *Attorney, Agent, or Firm* — Bayramoglu Law Offices LLC

(57) ABSTRACT

A chairless chair exoskeleton in order to provide seating support to the user while the user is standing particularly in industrial field includes at least one foot connection element for being connected to the foot of the user and at least one calf support element connected to said foot connection element, and at least one thigh support element connected to said calf support element by means of at least one joint and at least one energy storage element associated to the thigh support element from one side and associated to the calf support element from the other side.

6 Claims, 3 Drawing Sheets

(56) References Cited

U.S. PATENT DOCUMENTS

| | | | |
|---|---|---|---|
| 10,993,861 B2* | 5/2021 | Bae | A47C 9/10 |
| 2015/0005686 A1* | 1/2015 | Kazerounian | A61F 5/0123 |
| | | | 602/16 |
| 2016/0213549 A1* | 7/2016 | Iida | A61F 5/0125 |
| 2020/0155264 A1* | 5/2020 | Waterman | A61B 90/05 |
| 2021/0161750 A1* | 6/2021 | Aoki | A61H 3/00 |
| 2023/0240932 A1* | 8/2023 | Unal | B25J 9/0006 |
| | | | 601/5 |

* cited by examiner

CHAIRLESS CHAIR EXOSKELETON

CROSS REFERENCE TO THE RELATED APPLICATIONS

This application is the national phase entry of International Application No. PCT/TR2020/051456, filed on Dec. 30, 2020, the entire contents of which are incorporated herein by reference.

TECHNICAL FIELD

The present invention relates to at least one chairless chair exoskeleton in order to provide seating support to the user while the user is standing particularly in industrial field, and having at least one foot connection element for being connected to the foot of the user and at least one calf support element connected to said foot connection element, and at least one thigh support element connected to said calf support element by means of at least one joint and at least one energy storage element associated to the thigh support element from one side and associated to the calf support element from the other side.

BACKGROUND

Mechanical exoskeleton has been designed for supporting the person who wears it, for rehabilitating and/or for increasing performance thereof. For instance, mechanical exoskeleton is used for supporting and/or for increasing performance of soldiers or construction workers. Moreover, development of exoskeletons which can support movement of elderly people and individuals with muscle weaknesses or injuries, enables a wide medical market in the future. The other areas where advantage is provided are rescue works; heavy debris can be lifted by a lifeguard who wears this machine in collapsed buildings and at the same time, protection can be provided against falling taluses.

Assistive support devices are known in the art for different purposes and according to different categories. The exoskeletons developed for seating support are described as an apparatus including a connection unit for each leg and which supports the body weight of a person. Each unit includes a lower rod having an upper part and a lower part which can be extended longitudinally from the upper part. An upper rod is connected in a jointed manner to the upper end of the lower rod. The apparatus transfers the force due to weight of the person or a part of the weight of the person to the ground where the lower part is in contact. This apparatus has some limitations which shall be overcome by a characteristic of the present invention. Automatic control is not possible since the apparatus does not have active elements, brakes and damper.

As a result, because of the aforementioned problems, an improvement is required in the related technical field.

SUMMARY

The present invention relates to a chairless chair exoskeleton, for eliminating the aforementioned disadvantages and for bringing new advantages to the related technical field.

An object of the present invention is to provide a chairless chair exoskeleton developed for providing seating support to the user while the user is walking.

In order to realize the abovementioned objects and the objects which are to be deducted from the detailed description below, the present invention is at least one chairless chair exoskeleton in order to provide seating support to the user while the user is standing particularly in industrial field, and having at least one foot connection element for being connected to the foot of the user and at least one calf support element connected to said foot connection element, and at least one thigh support element connected to said calf support element by means of at least one joint and at least one energy storage element associated to the thigh support element from one side and associated to the calf support element from the other side. Accordingly, the improvement of the present invention is that the subject matter chairless chair exoskeleton includes at least one movement groove provided on the calf support element; an activation arm associated to the energy storage element from one side and positioned in a manner at least partially displacing in said movement groove from the other side; a locking arm connected from one side in a manner linearly displacing in the movement groove and which extends in a manner making downward protrusion from the foot connection element in the direction of the calf support element; and the locking arm is configured such that when one end of the locking arm presses to the ground, the other end of the locking arm fixes one end of the activation arm in the movement groove. Thus, the energy storage element is fixed for enabling providing of seating support to the user while the user is standing.

In a possible embodiment of the present invention, the activation arm is configured to provide the energy storage element to be in at least one free position by means of releasing from the resting of the locking arm as the user lifts his/her heel from the ground. Thus, walking support is provided to the user during walking.

In another possible embodiment of the present invention, the activation arm is configured to rotate in its own axis at least partially at both end parts. Thus, the linear movement of the locking arm can move the energy storage element between the free position and the support positions.

In another possible embodiment of the present invention, the foot embodiment of the locking arm is configured to contact the ground by means of at least one housing provided at the rear part at least partially. Thus, the locking arm contacts the ground.

In another possible embodiment of the present invention, at least one spring is provided which is configured to be able to drive the downward and upward directional movement of the locking arm. Thus, the locking arm moves in a linear manner in the movement groove.

REFERENCE NUMBERS

Figure 1:
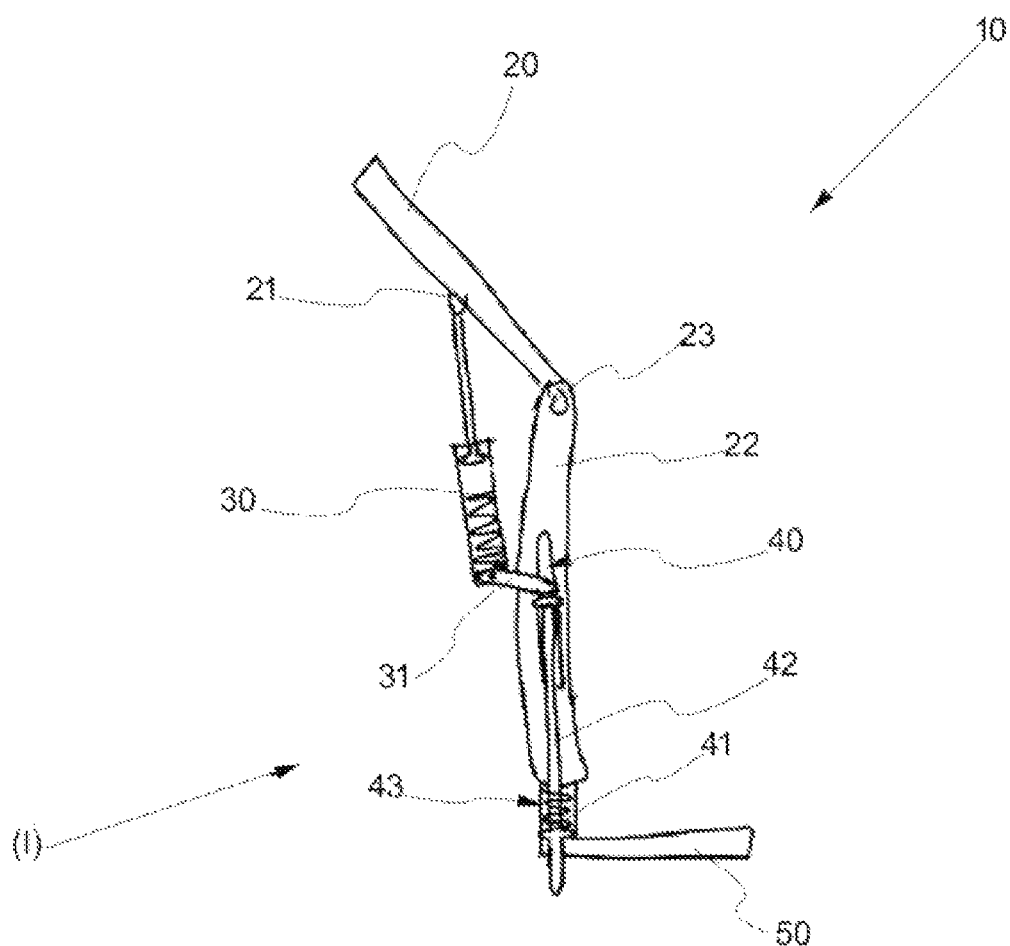
In FIG. 1, a representative perspective view where the subject matter chairless chair exoskeleton is at a free position is given.
Figure 2:
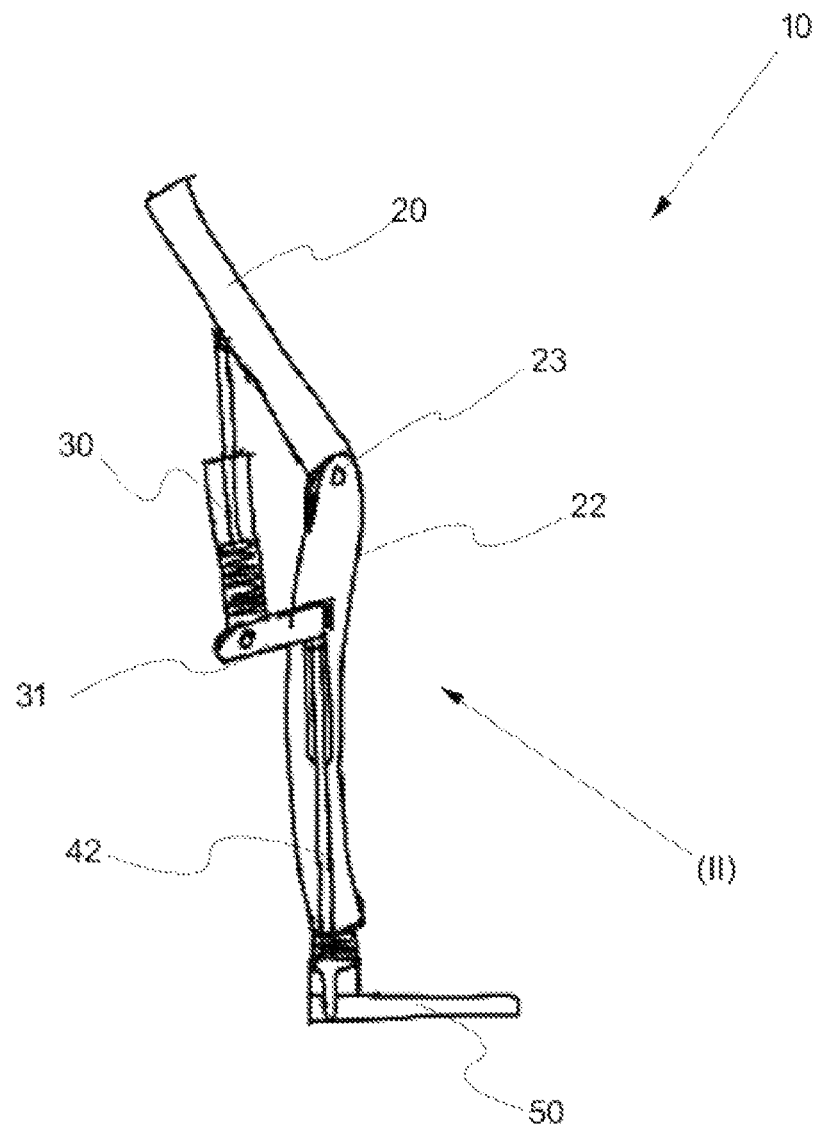
In FIG. 2, a representative perspective view where energy storage is enabled by means of fixing an energy storage element in the subject matter chairless chair exoskeleton is given.
Figure 3:
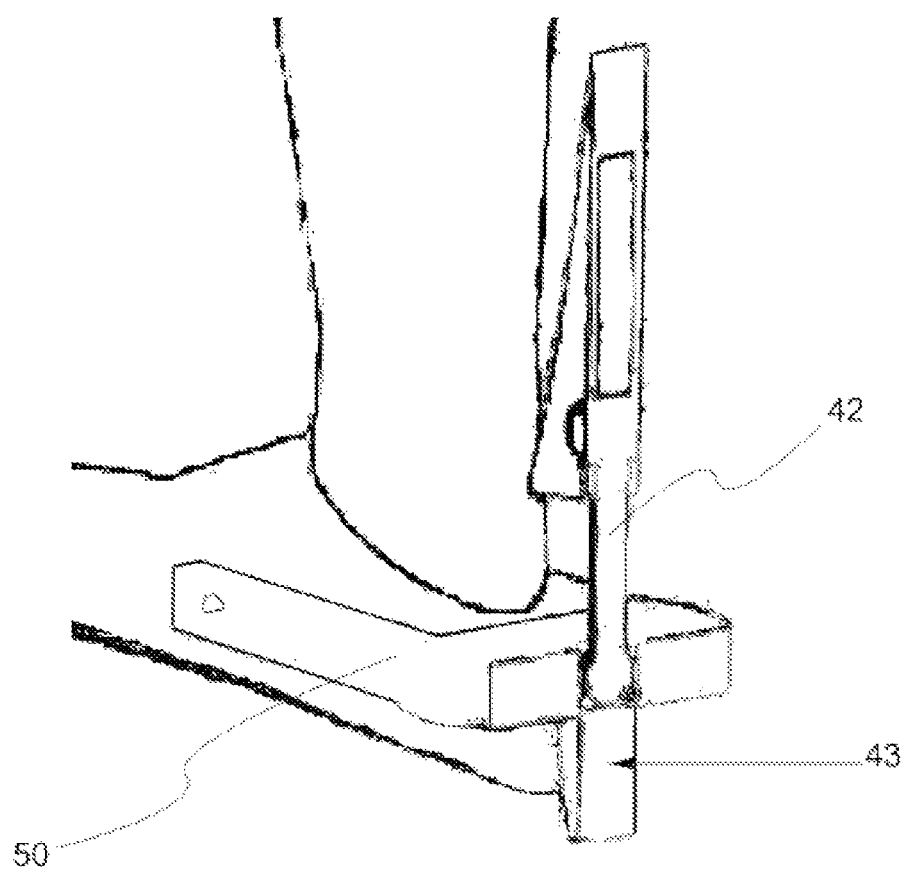
In FIG. 3, a representative perspective view of a foot connection element in the subject matter chairless chair exoskeleton is given.

10 Chairless chair exoskeleton
20 Thigh support element
21 First connection point
22 Calf support element
23 Joint 30 Energy storage element
31 Activation arm
40 Movement groove
41 Spring
42 Locking arm
43 Housing
50 Foot connection element
(I) Free position
(II) Support position

DETAILED DESCRIPTION OF THE EMBODIMENTS

In this detailed description, the subject matter chairless chair exoskeleton (10) is explained with references to examples without forming any restrictive effect only to make the subject more understandable.

In FIG. 1, a representative perspective view where the subject matter chairless chair exoskeleton (10) is at a free position (I) is given. Accordingly, said chairless chair exoskeleton (10) is a mechanical exoskeleton developed for providing support of seating to the users while the users are standing who have to continuously work by standing particularly in industrial works. The chairless chair exoskeleton (10) includes at least one thigh support element (20). The thigh support element (20) is a support element positioned essentially at the rear part of the upper leg region of the user and which provides supporting of the thigh bone. The chairless chair exoskeleton (10) includes at least one calf support element (22). Said calf support element (22) is essentially a calf support element connected to the lower leg part of the user. The chairless chair exoskeleton (10) includes at least one foot connection element (50). Said foot connection element (50) essentially provides connection from the rear part of the ankle joint and/or heel of the user. The foot connection element (50) is essentially a holder having two arms provided in C form. As the foot connection element (50) is connected from the rear part of the foot, the chairless chair exoskeleton (10) can be orthogonally positioned.

The thigh support element (20) is associated with the calf support element (22) by means of at least one joint (23). Said joint (23) is a joint for providing connection of the thigh support element (20) and the calf support element (22) to each other essentially in a manner providing rotational movement in between. The joint (23) is configured to be provided at the rear part of the knee. The chairless chair exoskeleton (10) includes at least one energy storage element (30). Said energy storage element (30) is essentially positioned between the thigh support element (20) and the calf support element (22). The energy storage element (30) is associated with the thigh support element (20) in at least one first connection point (21). Said first connection point (21) is a joint essentially provided on the thigh support element (20) and which provides connection of the energy storage element (30) and the thigh support element (20) in an at least partially rotatable manner. The energy storage element (30) provides supporting of the thigh support element (20).

The chairless chair exoskeleton (10) includes at least one movement groove (40). Said movement groove (40) is essentially an advancement housing (43) provided in the calf support element (22). The chairless chair exoskeleton (10) includes at least one activation arm (31). Said activation arm (31) is associated with the energy storage element from one side and is positioned in a manner displacing at least partially linearly in said movement groove (40) from the other side. The energy storage element (30) is connected to the activation arm (31) in a manner allowing rotation thereof in its own axis. The chairless chair exoskeleton (10) includes at least one locking arm (42). Said locking arm (42) is connected from one end in a manner moving linearly in the movement groove (40). The locking arm (42) is a rod essentially for drive. The locking arm (42) is provided in the direction of the calf support element (22) and in a manner making downward protrusion from the foot connection element (50). The foot connection element (50) essentially includes at least one housing (43) on the side which is close to the rear part. The locking arm (42) forms a protrusion by means of passing through the housing (43). The locking arm (42) co-operates with at least one spring (41) connected in the housing (43). Said spring (41) is a resetting element for providing forcing of the locking arm (42) to downward directional movement.

When one end of the locking arm (42) presses the ground, the other end of the locking arm (42) is manipulated to fix an end of the activation arm (31) in the movement groove (40). As one end of the locking arm (42) applies pressure to the ground, the locking arm (42) is compressed in its upward movement. As one end of the activation element is fixed in the movement groove (40), the energy storage element (30) is fixed, and thereby, the energy storage element (30) is provided at a support position (II) where energy can be stored. In said support position (II), the user realizes the seating action and realizes the weight acceptance support by means of the thigh support element (20). As one end of the locking arm (42) separates from the ground and as the compressed spring (41) returns the stored energy, the locking arm (42) protrudes downwardly from the foot connection element (50). As the end of the activation arm (31) positioned in the movement groove (40) is released, it is allowed that the energy storage element (30) is provided in a free position (I). In said free position (I), the energy storage element (30) realizes free movement and the energy storage function cannot be realized. Thus, since energy is not stored, the energy storage element (30) is deactivated, the knee freely rotates. This release is required for not preventing the free flexion of the knee. The free position (I) provides realization of ergonomic walking movements of the user during walking.

By means of all these embodiments, the chairless chair exoskeleton (10) provides supporting of the user from the thigh part for providing seating sense in case of standing of the user during working and in case of waiting of the user. As the functions of the energy storage element (30) between the free position (I) and the support positions (II) change, it is enabled to provide walking support to the user. The chairless chair exoskeleton (10) provides an ergonomic usage. It provides freedom to the knee to realize its natural movements during walking.

The protection scope of the present invention is set forth in the annexed claims and cannot be restricted to the illustrative disclosures given above, under the detailed description. It is because a person skilled in the relevant art can obviously produce similar embodiments under the light of the foregoing disclosures, without departing from the main principles of the present invention.

What is claimed is:

1. A chairless chair exoskeleton in order to provide a seating support to a user while the user is standing particularly in an industrial field, comprising at least one foot connection element for being connected to a foot of the user, and at least one calf support element connected to the at least one foot connection element, and at least one thigh support element connected to the at least one calf support element by means of at least one joint and at least one energy storage element, wherein the at least one energy storage element is associated to the at least one thigh support element from a first side and associated to the at least one calf support element from a second side, wherein the subject matter chairless chair exoskeleton comprises at least one movement groove provided on the at least one calf support element;

an activation arm, wherein the activation arm is associated to the at least one energy storage element from one side and positioned in a manner at least partially displacing in the at least one movement groove from another side;

a locking arm, wherein the locking arm is connected from one side in a manner linearly displacing in the at least one movement groove, and the locking arm extends in a manner making a downward protrusion from the at least one foot connection element in a direction of the at least one calf support element; and the locking arm is configured that when a first end of the locking arm presses to the ground, a second end of the locking arm fixes one end of the activation arm in the at least one movement groove.

2. The chairless chair exoskeleton according to claim 1, wherein the activation arm is configured to provide the at least one energy storage element to be in at least one free position by means of releasing from a resting of the locking arm as the user lifts his/her heel from the ground.

3. The chairless chair exoskeleton according to claim 1, wherein the at least one energy storage element is connected to the locking arm in a movable manner by means of at least one activation arm.

4. The chairless chair exoskeleton according to claim 1, wherein the activation arm is configured to rotate in an axis of the activation arm at least partially at two end parts.

5. The chairless chair exoskeleton according to claim 1, wherein a foot embodiment of the locking arm is configured to contact the ground by means of at least one housing provided at a rear part at least partially.

6. The chairless chair exoskeleton according to claim 1, wherein at least one spring is provided, and the at least one spring is configured to drive a downward and upward directional movement of the locking arm.

* * * * *